United States Patent [19]

Gula et al.

[11] 4,447,230
[45] May 8, 1984

[54] INTRAVENOUS ADMINISTRATION SET ASSEMBLY

[75] Inventors: John A. Gula, Richardson; John D. Brady, Dallas; Thomas C. Thompson, McKinney; Joyce M. Alt, Houston, all of Tex.

[73] Assignee: Quest Medical, Inc., Carrollton, Tex.

[21] Appl. No.: 290,257

[22] Filed: Aug. 5, 1981

[51] Int. Cl.³ ............................................. A61M 1/00
[52] U.S. Cl. ................................... 604/122; 604/247; 604/126; 604/411
[58] Field of Search ............ 128/214 R, 214 C, 214 E, 128/214 F, 214 G, 214.2, DIG. 12, 202.27; 137/605, 606; 222/145; 248/318, 122, 125, 226.4; 604/80–86, 122, 126, 411, 247; 285/45, 332

[56] References Cited

U.S. PATENT DOCUMENTS

| | | | |
|---|---|---|---|
| 3,043,303 | 7/1962 | Still | 604/66 |
| 3,677,248 | 7/1972 | McPhee | 604/122 |
| 3,886,937 | 6/1975 | Bobo et al. | 222/145 |
| 3,941,126 | 3/1976 | Dietrich et al. | 128/214.2 |
| 4,005,844 | 2/1977 | Richmond | 248/318 |
| 4,258,712 | 3/1981 | Harms et al. | 604/81 |
| 4,296,949 | 10/1981 | Muetterties et al. | 285/332 |
| 4,324,238 | 4/1982 | Genese et al. | 222/145 |
| 4,334,538 | 6/1982 | Juhn | 128/276 |

Primary Examiner—C. Fred Rosenbaum
Assistant Examiner—J. L. Kruter
Attorney, Agent, or Firm—Isaksen, Lathrop, Esch, Hart & Clark

[57] ABSTRACT

An intravenous administration set assembly (10) is disclosed which is capable of introducing fluid from a plurality of sources of intravenous fluids into a patient and which allows the various sources of fluid to be easily attached and detected from the assembly without the necessity for intravening safety steps, such as purging the system, and yet without any possibility of air or bacteria being introduced through the system into the patient. An air-eliminating filter (32) is attached to a manifold formed of fittings (26) which are connected through inlet adapters (28) to the sources of intravenous fluid. The air-eliminating filter (32) ensures that air or bacteria introduced into the assembly (10) through attaching or detaching sources to the assembly does not pass to the patient and also ensures that a head pressure is maintained relative to the venous pressure of the patient to prevent a back flow of blood from the patient into the assembly. Check valves are provided in each of the inlet adapters (28) attached to the manifold fittings (26) to prevent back flow from any one of the sources of fluid into another one of the sources to thus prevent contamination of the sources.

12 Claims, 3 Drawing Figures

INTRAVENOUS ADMINISTRATION SET ASSEMBLY

BACKGROUND OF THE INVENTION

The present invention relates to intravenous administration sets in general and, in particular, to intravenous administration set assemblies particularly adapted to allow the administration of multiple types of intravenous solutions into a patient, either sequentially or simultaneously.

DESCRIPTION OF THE PRIOR ART

The prior art is generally cognizant of the concept of introducing multiple types of intravenous fluid into a patient from two different sources through a common intravenous set assembly. Thus, for example, U.S. Pat. No. No. 4,257,416 discloses a multi-channel infusion set which is designed to mix fluids from three different sources into a common conduit connected so as to infuse fluids into the patient.

It has become common practice in many hospitals wherein it is desired to introduce volumes of different chemicals into a patient, such as is often required in chemotherapy, to form multiple source intravenous administration sets by connecting a variety of containers of intravenous solutions containing these chemicals to each other through three-way stop cocks all interconnected by plastic tubing. Each of the lengths of tubing connected to each source of fluid must then also be provided with a valve so that each individual source of fluid can be turned on or off to properly sequence the solutions. The entire assembly is then manually manipulated by a nurse or other attendant so as to allow fluid flow from each container sequentially or simultaneously as is desired. Such improvised assemblies are characterized by the fact that they do not commonly use standard fittings which can be interconnected to each other and do not provide any mechanism for detaching or attaching new fluid sources to the assembly, during its operation, without the necessity for purging the entire assembly to prevent the introduction of air into the patient. Such assemblies are also typically characterized by a large amount of excess tubing which often gets tangled, which keeps the patient from becoming ambulatory, and which makes proper operation of the assembly difficult because of the necessity for keeping track of the valves in each of the tubes and the necessity to keep the patient in one position to avoid tangling of the tubing. These systems can also, after the fluid containers run dry, allow fluid to drain down to a very low level within the tubing connected to the patient so that, on occasion, back flow from the patient's venous pressure can cause some of the patient's blood to be forced into the bottom portion of the intravenous assembly, thereby raising the possibility of blood clotting in the assembly. Prior art systems also usually have no provision for keeping bacteria from being introduced into the system by couplings or uncouplings of system parts from passing into the patient.

Some manufacturers currently offer intravenous filtration systems including therein a provision for, at most, two different sources of fluid flowing to the patient through a common air-eliminating filter. One such system is currently offered for sale by Travenol Laboratories, Inc. That system includes a pair of drip chambers having their outputs simply connected together and connected to an air-eliminating filter feeding to the patient. No prior system is known which includes a manifold and air filter combination capable of allowing more than two fluid sources to be connected together for sequential infusion into a patient and none is known which includes structure designed to prevent intercontamination between the various fluid sources.

SUMMARY OF THE INVENTION

The present invention is summarized in that an intravenous administration set assembly includes: an adapter adapted for mating with a corresponding adapter provided on a catheter inserted into a patient; an air-eliminating filter capable of receiving an air and fluid mixture through its inlet and separating the air therefrom so that only fluid may pass through its outlet; tubing means connecting the outlet of the air-eliminating filter to the adapter; a fluid manifold having a plurality of inlets and a single outlet, the outlet of the fluid manifold being connected to the inlet of the air-eliminating filter; and an inlet adapter connected to each of the inlets of the fluid manifold so as to admit fluid thereto, each of the inlet adapters including a standardized mating connector thereon so that it is capable of being securely mated in a fluid-tight fashion to tubing connected from a source of intravenous fluid, and at least one check valve connected so as to allow fluid to pass through the fluid manifold from the inlet adapters and to prevent the flow of fluid outward from the fluid manifold through the inlet adapters and so as to prevent the contamination of one of the sources of intravenous fluid connected to the manifold by another of those sources of intravenous fluid.

It is an object of the present invention to provide an intravenous administration set assembly which is capable of receiving fluid from a plurality of sources of intravenous fluid and introducing all of the fluids into the patient without air passing therethrough and without intercontamination among the various fluid sources.

It is yet another object of the present invention to provide such a multi-source intravenous administration set in which it is possible to connect and detach fluid sources from the system during its operation without any necessity for purging the system following any such attachment or detachment and without any necessity for interrupting fluid flow to the patient.

It is yet another object of the present invention to provide such a multi-source intravenous administration set which includes structure sufficient to insure so that back flow from the patient into the intravenous administration set is eliminated by maintaining a sufficient fluid head at all times so that the patient's venous pressure cannot cause back flow of blood into the intravenous set.

Other objects, advantages, and features of the present invention will become apparent from the following specification when taken in conjunction with the accompanying drawings.

DESCRIPTION OF THE PREFERRED EMBODIMENT

Figure 1:
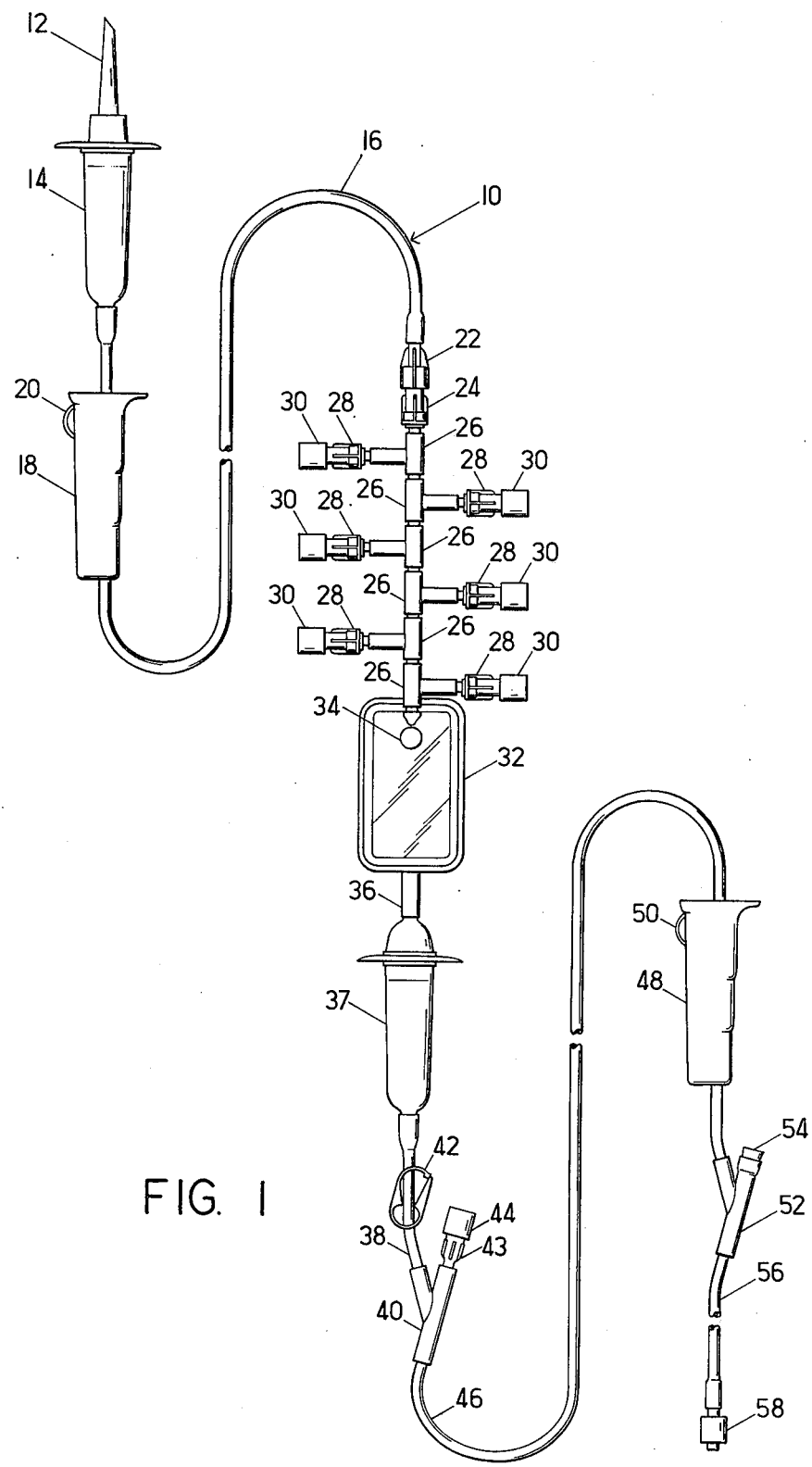
FIG. 1 is a plan view of an intravenous administration set assembly constructed in accordance with the present invention.

Shown in FIG. 1, and generally illustrated at 10, is a multiple source intravenous administration set assembly constructed in accordance with the present invention. At one end, the set 10 has formed on it a standard IV bag fitting 12 which is connected to a transparent, vertically elongated drip chamber 14. At its lower end, the drip chamber 14 is connected to one end of a section of PVC intravenous feeding tubing 16. Mounted on the tubing 16 is a roller clamp 18 which is operated by a thumbwheel roller 20 so as to be capable of clamping and unclamping the tubing 16. At its lower end, the intravenous tubing 16 is provided with a male luer lock adapter 22. The male luer lock adapter 22 is threadedly engaged onto a female luer lock adapter 24. The female luer lock adapter 24 is attached, in turn, to one of a series of tee fittings 26. In the embodiment of FIG. 1, there are six of the tee fittings 26, each of which, except the last one, is attached at its other end to the next adjacent tee fitting 26. Alternate ones of the tee fittings 26 are oriented with the arm of the tee directed in opposite directions so that three tee fittings 26 point in each direction. The assemblage of the six tee fittings 26 thus forms a continuous manifold having three arms directed oppositely from three other arms. On each of the arms of the manifold formed by the assembly of the tee fittings 26, there is attached a respective female luer lock adapter 28. The female luer lock adapters 28 are inlet adapters to the seven inlets into the manifold of fittings 26, and each of the adapters 28 includes both a mating luer connection and a locking mechanism to both mate to a corresponding fitting and to lock two mated fittings together. Each of the female luer lock adapters 28 also includes therein an integrally formed check valve, not shown in greater detail in FIG. 1. The check valve in each of the female luer lock adapters 28 takes the form of a flap of semi-flexible material mounted on the interior of the respective female luer lock adapter 28 and secured to the periphery of the interior of the luer lock adapter 28 only on one side thereof to thus function as a flap valve allowing fluid flow in only one direction, with that direction being into the manifold of fittings 26. Threaded onto the exterior of each of the female luer lock adapters 28 is a lock cover 30. Each of the lock covers 30 has an interior surface similar in configuration to the interior of a male luer lock adapter but has a plain exterior surface. The lock covers 30 are designed to protect the exterior of the female luer lock adapters 28 from contamination from the exterior environment when they are not connected to a mating adapter.

Mounted on the bottom of the manifold formed by the tee fittings 26 and attached to the lowermost one of the tee fittings 26, which serves as a single outlet for the manifold of fittings 26, is a 0.22 micron air-eliminating fluid filter 32. The air-eliminating filter 32 includes therein separate hydrophobic and hydrophilic membranes designed to allow fluid to pass through the filter 32 while air is passed out of the filter 32 through an air exit port 34. The air-eliminating filter 32 also has sufficiently small filter openings that bacteria may not pass through it. At the bottom exit of the air-eliminating filter 32, an exit fitting 36 is attached to a fluid flow monitoring station in the form of a drip chamber 37.

The other end of the drip chamber 37 is attached to one end of a section of PVC tubing 38, the other end of which is attached to a Y-fitting 40. A thumb operated snap lock 42 is entrained onto the tubing 38 so as to selectably pinch the tubing 38 closed. The Y-fitting 40 has the other arm of its Y attached to a female luer lock adapter 43 having a lock cover 44 provided thereon. The base of the Y formed by the Y-fitting 40 is connected to one end of another section of tubing 46 which is connected at its other end to a Y-fitting 52. A roller clamp 48 is entrained on the section of tubing 46 and includes a thumbwheel roller 50 provided thereon so as to be manually operable. The other arm of the Y-fitting 52 includes an injection site 54 formed thereon by a piece of elastic membrane stretched over the open end of the arm of the Y-fitting 52. The base of the Y of the Y-fitting 52 is attached to a section of tubing 56 at one end thereof with the other end of the tubing 56 being connected to a male luer lock adapter 58.

The multiple source intravenous set assembly 10 shown in FIG. 1 is intended for use in a hospital environment in which it is desired to introduce a variety of biological fluids into a patient. A multiple-source infusion is often desired in hospitals conducting cancer chemotherapy or other therapies involving the transfusions of various diverse drugs serially into a patient, with the drugs typically being intravenously metered into the patient by dilution in saline solutions in conventional intranveous solution bags. The intravenous set assembly 10 allows a plurality of intravenous bags to be attached and detached from the assembly 10 without the need for purging of the system upon the addition or removal of any bag, and without the need to worry about the bags emptying and allowing the patient's venous pressure to force blood back into the intravenous assembly 10, while still allowing the physician to select the order in which drugs are infused into the patient, and while insuring that air and bacteria are never introduced into the patient intravenously through the system. By adjusting the relative heights of the sources of fluid, the order in which the fluids flow into the patient can be selected without any of the fluids becoming intermixed since the fluid pressure from the highest bag tends to close the check valves connected to the other bags. The use of the intravenous assembly 10 also allows the rate of cumulative flow of fluid into the patient to be monitored at one single location, i.e. anywhere below the manifold 26, an objective which cannot easily be done with conventional multi-source intravenous administration systems in which multiple containers are introducing fluid into a patient. These beneficial results are inherently achieved because of the novel structure disclosed here and the beneficial results flowing therefrom.

Figure 2:
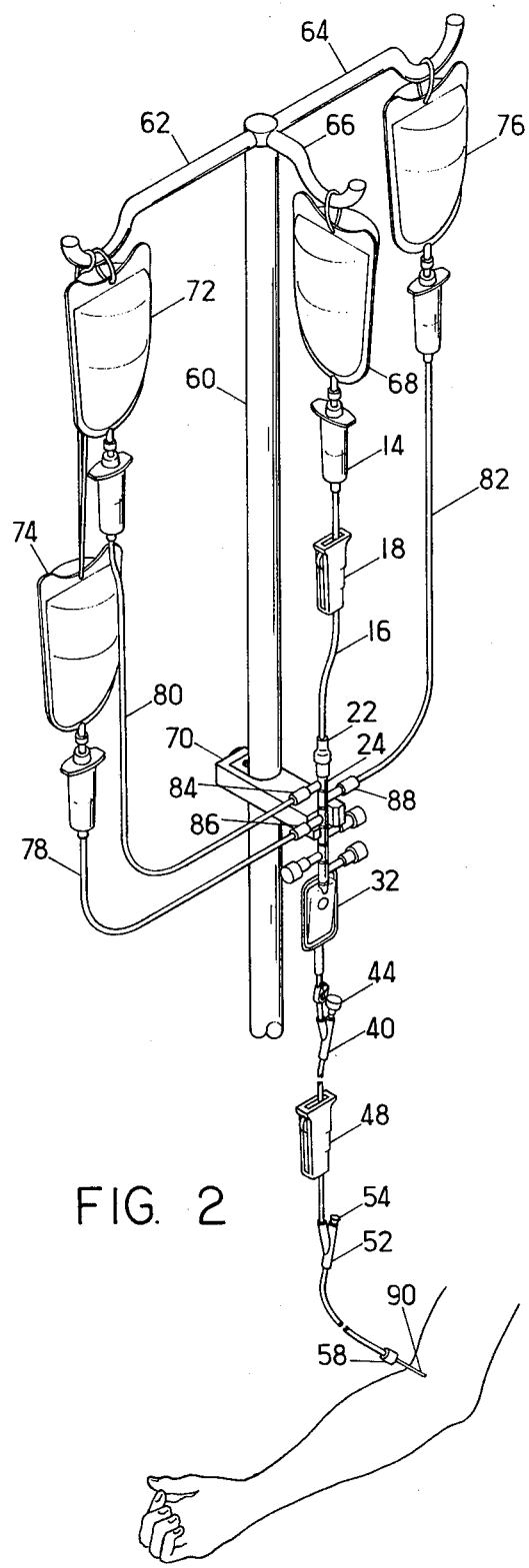
FIG. 2 is a perspective view of a typical installation showing the use of the intravenous administration set assembly of FIG. 1.

The operation of the intravenous assembly 10 can now be described with reference to FIG. 2, which shows the apparatus in use delivering fluid to a patient. The entire assembly 10 is mounted on a conventional IV mounting pole 60 used for hanging IV assemblies. The pole 60, as shown in FIG. 2, has three arms indicated at 62, 64, and 66, although it is envisioned that a conventional two-armed pole or a pole having any other number of suitable arms could easily be utilized in the present invention. The drip chamber 14 has its fitting 12 inserted into the corresponding fitting formed on a main intravenous solution supply bag 68. The bag 68 is suspended from the arm 66, just adjacent the arm 66 itself, and the remaining parts of the assembly 10 dangle downward from the bag 68 to the point at which a clamp 70 is mounted on the pole 60. The clamp 70 is configured specifically to hold the manifold formed by the tee fittings 26, as will be described in detail later. Looped onto the arm 62 of the pole 60 are two intravenous solution bags 72 and 74 which have diluted solutions of drugs contained therein. The bag 72 is suspended just underneath the arm 62 while the bag 74 is suspended some distance below the arm 62. The bags 72 and 74 are connected to drip chambers provided at their lower ends which are connected, in turn, through tubes 80 and 78 to respective male luer lock adapters 84 and 86 which are threadedly received on a pair of the female luer lock adapters 28 provided on the assembly 10. Similarly, an intravenous solution bag 76, suspended just beneath the arm 64, having a solution of another drug therein is connected by a tube 82 to a male luer lock fitting 88 which is threaded onto another of the female luer lock adapters 28 provided on the opposite side of the manifold formed by the tee fittings 26 of the assembly 10. The remaining components of the IV assembly 10 dangle downward from the clamp 70. The male luer lock adapter 58 is threadedly received over a corresponding adapter mounted on a catheter 90 inserted into the arm of the patient.

Figure 3:
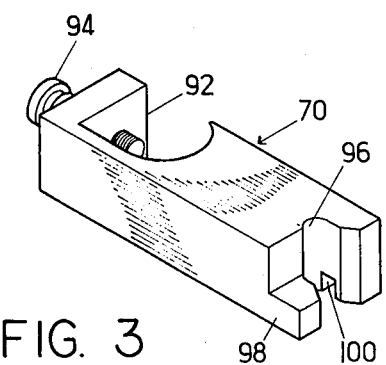
FIG. 3 is a perspective view of a clamp used in the installation of the intravenous administration set assembly as shown in FIG. 2.

Shown in FIG. 3 are the details of the clamp 70 which is used to mount the assembly 10 on the pole 60. The clamp 70 includes an open-sided cavity 92 sized to fit around the pole 60 and a manually operable screw 94 extending into the cavity 92 so that the screw 94 can be tightened to fix the clamp 70 on the pole 60 at any desired location thereon. At its front end, the clamp 70 includes a vertical channel 96 designed and sized to receive any portion of the vertical extent of the manifold formed by the fittings 26. A support arm 98 extends forwardly from the clamp 70 adjacent the vertical channel 96 and a transverse channel 100 extends transversely from the channel 100 adjacent the forward edge of the clamp 70 along the bottom thereof. When the assembly 10 is mounted on the clamps 70, the manifold of the fittings 26 is placed with one of its vertical sections in the vertical channel 96 while one transerse arm of one of the tee fittings 26 is received on top of the arm 98 while another extends through the transverse channel 100. Thus, the clamp 70 allows the assembly 10 to be suspended from the pole 60 by virtue of the clamp 70 holding the manifold of fittings 26. Since the front end of the clamp 70 is particularly configured to receive the manifold 26, the assembly 10 is relatively securely mounted and protected from being dislodged while still allowing the assembly 10 to be easily removed and replaced.

The intravenous administration set assembly 10 of FIGS. 1-3 allows the nurse or other attendant to easily and safely set up a multiple source infusion apparatus for a patient with the order of the introduction of the various different fluids being easily selectable. The order of infusion of the different solutions is selected simply through the relative vertical positioning of the solution containers. Thus, in the example of FIG. 2, the solutions from bags 68, 72 and 76 will first all simultaneously diffuse into the patient with the contents of the bag 74 starting infusion only when all the bags 68, 72 and 76 are empty. This order occurs simply because the head pressure is higher in the bags 68, 72 and 76, thus keeping the check valve in the adapter 28 to which the bag 74 is attached closed. The check valve in that adapter 28 also serves to prevent any unwanted contamination of the solution in the bag 74 by preventing fluid from flowing into the bag 74 from the manifold 26 while there is fluid in the bags 68, 72 and 76. At the same time, regardless of which bags are emptying into the patient and how many bags are simultaneously emptying, the combined rate of fluid flow can be measured at a single location. Thus, at the drip chamber 37, it is possible to monitor the combined fluid flow through the assembly 10. It is also envisioned that the drip chamber 37 could be replaced by any other suitable fluid flow monitoring device.

The female luer lock adapter 43 and the Y-fitting 40 serve as a connection point through which whole blood can be given to the patient. This state is located below the filter 32 since whole blood should not be filtered through the filter 32. The injection site 54 is provided on the fitting 52 so that immediate injections can be given the patient through the assembly 10. Alternatively, the injection site 54 can be used for withdrawal of blood samples from the patient if the clamp 48 is clamped and blood withdrawn through the catheter 90 and the tubing 56.

The assembly 10 allows different solutions to be added to or removed from the assembly 10 without any particular precautions for air or bacteria introduction being taken. Since the air-eliminating filter 32 prevents air, and bacteria, from passing therethrough, additional fittings can be simply added to, or removed from, the assembly 10 without worrying about the introduction of bacteria or air. Thus, the changing of solutions for a patient is extremely easy, while complete safety for the patient is maintained.

Furthermore, the air-eliminating filter 32 provides one more advantage. Since air cannot pass therethrough, there is fluid just underneath the filter 32 at all times once the assembly is first filled. Since the filter 32 is mounted relatively high on the assembly 10, just underneath the clamp 70 and the manifold of fittings 26, and since there will always be a fluid head at least as high as the filter 32, the assembly 10 will maintain a higher fluid head pressure than the blood pressure of the patient, thus preventing blood flow from the patient back into the lower part of the assembly 10 if the sources of fluid were empty and the patient's blood pressure increased. Such back flows of blood can occur in other IV sets and can lead to clotting or contamination of the sets, a problem avoided with the assembly here.

Thus, the intravenous set assembly 10 of FIGS. 1-3 functions as an easily usable assembly capable of introducing a variety of different sources of intravenous fluid to a patient. The assembly 10 allows the use of a large number of sources of fluid and provides a standard, quick, convenient and secure connection of each source to the assembly. This convenience is equally matched by provisions for the patient's safety to prevent air or bacteria from being introduced to the patient and to prevent back flow of the patient's blood.

It is understood that the present invention is not limited to the particular arrangement of parts disclosed and illustrated herein but includes all such modified forms thereof as come within the scope of the following claims.

We claim:

1. An intravenous administration set assembly capable of use with at least three differing sources of intravenous fluid comprising:

adapter means (58) for mating with a corresponding adapter provided on a catheter (90) inserted into a patient;

air-eliminating filter means (32) having a hydrophilic membrane completely across the fluid flow path for receiving an air and fluid mixture through its inlet and separating the air therefrom so that only fluid may pass through its outlet;

tubing means (38, 46, 56) connecting the outlet of the air-eliminating filter means (32) to the adapter means (58);

fluid manifold means (26) having at least three inlets and a single outlet to allow for the sequencing of differing fluids from their respective sources, the outlet of the fluid manifold means (26) being connected to the inlet of the air-eliminating filter means (32) so that all fluid flowing from the outlet of the fluid manifold means must pass through the air-eliminating filter means regardless of the source of the fluid;

inlet adapter means (28) connected to each of the inlets of the fluid manifold means (26) so as to admit fluid thereto, each of the inlet adapter means (28) including a mating connector thereon so that it is securely mated in fluid-tight fashion to tubing connected from a respective one of the sources of intravenous fluid; and one check valve means for each and every adapter means (28) connected so as to allow fluid to pass through the fluid manifold means (26) from the inlet adapter means (28) and so as to prevent the flow of fluid outward from the fluid manifold means (26) through the inlet adapter means (28) and so as to prevent the contamination of one of the sources of intravenous fluid connected to the manifold means (26) by another of those sources of intravenous fluid.

2. An intravenous administration set assembly as claimed in claim 1 wherein the tubing means (38, 46, 56) connected between the air-eliminating filter (32) and the adapter (58) includes at least one fitting (52) having an injection site (54) provided therein so that injections of medication to the patient can easily be made in the course of intravenous administrations of fluid to a patient.

3. An intravenous administration set assembly as claimed in claim 2 wherein the tubing means (38, 46, 56) further includes a second fitting (40) having an inlet adapter (43) provided thereon which is capable of being locked to a source of biological fluid for introduction to a patient which may not pass through an air-eliminating filter.

4. An intranvenous administration set assembly as claimed in claim 1 wherein each of the inlet adapters (28) also includes a locking mechanism so that a pair of the mated adapters can be securely locked together.

5. An intravenous administration set assembly as claimed in claim 4 wherein each of the inlet adapters (28) is a female luer lock adapter capable of providing a secure lock to a corresponding male luer lock adapter.

6. An intravenous administration set assembly for use with multiple sources of intravenous fluid comprising:
an adapter (58) adapted for mating with a corresponding adapter provided on a catheter (90) inserted into a patient;
an air-eliminating filter means (32) capable of receiving an air and fluid mixture through its inlet and separating the air therefrom so that only fluid may pass through its outlet;
tubing means (38, 46, 56) connecting the outlet of the air-eliminating filter (32) to the adapter (58);
a fluid manifold (26) having at least three inlets and a single outlet, the outlet of the fluid manifold (26) being connected to the inlet of the air-eliminating filter (32) so that all fluid flowing from the outlet of the fluid manifold must pass through the air-eliminating filter regardless of the source of the fluid;
an inlet adapter (28) connected to each of the inlets of the fluid manifold (26) so as to admit fluid thereto, each of the inlet adapters (28) including a standardized female Luer lock mating connector theron so that it is adapted to being securely mated in fluid-tight fashion to a corresponding male Luer lock adapter on tubing connected from a respective one of the sources of intravenous fluid;
one check valve for each and every adapter (28) connected so as to allow fluid to pass through the fluid manifold (26) from the inlet adapters (28) and to prevent the flow of fluid outward from the fluid manifold (26) through the inlet adapters (28) and so as to prevent the contamination of one of the sources of the intravenous fluid connected to the manifold (26) by another of those sources of intravenous fluid;
each of the inlet female Luer lock adapters (28) being initially provided with a corresponding lock cover (38) received thereover so as to prevent contamination thereof.

7. An intravenous administration set assembly as claimed in claim 1 therein the assembly (10) is mounted above the patient and wherein the filter (32) is located just underneath the manifold (26) so that a fluid head is maintained at all times at least as high as the filter (32) to prevent back flow of the patient's blood into the assembly.

8. An intravenous administration set assembly as claimed in claim 7 wherein the assembly (10) is suspended from a pole (60) by means of a clamp (70) secured to the pole (60), the clamp (70) being particularly adapted (86, 89, 100) to receive the manifold (26) so that the assembly can be suspended therefrom.

9. An intravenous administration set assembly for use with multiple sources of intravenous fluid comprising:
adapter means (58) for mating with a corresponding adapter provided on a catheter (90) inserted into a patient;
fluid manifold means (26) having at least three inlets and a single outlet, the manifold means (26) being suspended in a high position relative to the patient;
tubing means (38, 46, 56) connecting the manifold means (26) to the adapter means (58);
tubing means (16) adapted to connect at least one adapter means (58) to at least a first one of the sources of intravenous fluid;
check valve means connected to each inlet to the manifold (26) to prevent back fluid flow therethrough; and
air-eliminating filter means (32) mounted just underneath the manifold means (26) and connected between the manifold means (26) and the tubing means (38, 46, 56) so that all fluid flow through the manifold means (26), regardless of source, must pass through the air-eliminating filter means (32), the air-eliminating filter means (32) including therein a hydrophilic membrane in the path of fluid flow thereby preventing air flow therethrough and thus maintaining a fluid head in the tubing means (38, 46, 56) sufficient so as to prevent back flow of the patient's fluid into the assembly.

10. An intravenous administration set assembly as claimed in claim 9 wherein a pole (60) has the assembly (10) mounted thereon and wherein a clamp (70) is locked to the pole (60), the clamp (70) being shaped (96, 98, 100) to receive and support the manifold (26) so as to suspend the manifold (26) in place from the pole (60).

11. An intravenous administration set assembly as claimed in claim 9 wherein each of the inlets to the manifold (26) includes an adapter (28) having a check valve provided therein to prevent unwanted fluid flow between different fluid sources.

12. An intravenous administration set assembly as claimed in claim 11 wherein each of the adapters (28) also includes a female luer lock formed on the exterior thereof so as to be easily and securely lockable to a source of intravenous solution.

* * * * *